United States Patent [19]

Bottaro et al.

[11] Patent Number: 6,096,774
[45] Date of Patent: Aug. 1, 2000

[54] ENERGETIC NITRAMINE-LINKED AZOLES AND HYDROXYLAMMONIUM SALTS AS OXIDIZERS, INTIATORS AND GAS GENERATORS

[75] Inventors: Jeffrey C. Bottaro, Mountain View; Robert J. Schmitt, Palo Alto; Mark A. Petrie, Cupertino; Paul E. Penwell, Palo Alto, all of Calif.

[73] Assignee: SRI International, Menlo Park, Calif.

[21] Appl. No.: 09/168,308

[22] Filed: Oct. 7, 1998

[51] Int. Cl.$^7$ .................. A61K 31/4196; C07D 249/14
[52] U.S. Cl. .................. 514/383; 548/264.8; 548/265.2; 548/265.6; 548/267.2
[58] Field of Search .................. 548/264.8, 265.2, 548/265.6, 267.2; 514/383

[56] References Cited

U.S. PATENT DOCUMENTS

| | | |
|---|---|---|
| 3,636,001 | 1/1972 | Reisser et al. . |
| 3,709,920 | 1/1973 | McDowell et al. . |
| 3,714,199 | 1/1973 | McDowell et al. . |
| 3,714,200 | 1/1973 | McDowell et al. . |
| 3,883,374 | 5/1975 | Rosher . |
| 4,085,123 | 4/1978 | Flanagan et al. . |
| 4,527,389 | 7/1985 | Biddle et al. . |
| 5,014,623 | 5/1991 | Walker . |
| 5,274,105 | 12/1993 | Rothgery et al. . |
| 5,468,313 | 11/1995 | Wallace, II et al. . |
| 5,574,240 | 11/1996 | Cartwright . |

*Primary Examiner*—Patricia L. Morris
*Attorney, Agent, or Firm*—Dianne E. Reed; Reed & Associates

[57] ABSTRACT

Novel compounds are provided having the structural formula $R[-N(NO_2)-L-R^1]_n$ wherein R, L, $R^1$ and n are defined herein. The compounds are useful in a variety of contexts, but are primarily to be used as high energy oxidizing agents in explosive compositions, propellant formulations, gas-generating compositions and the like. The compounds are also useful as pharmaceutical agents. Compositions containing the compounds are also provided, including energetic compositions, as are methods for using the novel compounds and compositions.

10 Claims, No Drawings

ENERGETIC NITRAMINE-LINKED AZOLES AND HYDROXYLAMMONIUM SALTS AS OXIDIZERS, INTIATORS AND GAS GENERATORS

REFERENCE TO GOVERNMENT SUPPORT

This invention was funded in part by the United States Office of Naval Research under Contract No. N00014-95-C-0209 and in part by the United States Air Force Office of Scientific Research under Contract No. AF-F04611-96-K-0013. The United States Government has certain rights in this invention.

TECHNICAL FIELD

The present invention relates generally to energetic materials, and more particularly relates to novel chemical compounds useful, inter alia, as high energy oxidizing agents. Methods for using the novel compounds as oxidizing agents in energetic compositions are also provided, as are energetic compositions containing the compounds. In addition, the invention relates to use of the present compounds as pharmaceutical agents, e.g., as vasodilating agents.

BACKGROUND

"Energetic" compounds are used extensively in a wide variety of applications, e.g., in explosive formulations, propellants, gas-generating compositions, and the like. It is generally preferred that such materials have a high energy content yet be relatively insensitive to impact, such that accidents are avoided and energy is released only when intended. The requirements of insensitivity and high energy are in conflict, making the development of new energetic materials a difficult and challenging synthetic problem.

In developing new energetic compounds, a number of factors come into play. For example, heats of formation, density, melting and decomposition temperatures, carbon content and, generally, nitrogen content, are properties which must be considered. Energetic compounds should display good thermal and shock properties, have high heats of formation, and be straightforward to synthesize in bulk. It is generally preferred that an energetic compound have a melting point above about 100° C., an exothermic heat of combustion and a positive heat of formation $\Delta H_f$, and a high decomposition temperature, with a relatively large separation between melting point and decomposition temperature preferred such that an energetic composition may be melt cast from the selected compound. Finally, it is of course preferred that an energetic compound be relatively simple and straightforward to synthesize in high yield.

A number of energetic compounds are known as useful as oxidizers, explosives and the like. Energetic compounds have also been disclosed as useful to inflate automobile and aircraft occupant restraint bags. However, previously known materials are generally limited in one or more ways, e.g., they are overly impact-sensitive, difficult to synthesize on a large scale, not sufficiently energetic, or the like. In addition, energetic compositions used to inflate occupant restraint bags in automobiles and aircraft typically contain potentially toxic heavy metal igniter materials, e.g., mercury compounds, $Pb(N_3)_2$ or the like.

The present invention provides a new class of compounds which overcomes the aforementioned limitations in the art. The energetic compounds to which the invention pertains are commonly referred to as "secondary" explosives, i.e., compounds whose energy is released after activation by initiator compounds, also termed "primary" explosives. The compounds now provided herein meet all of the above-mentioned criteria, and outperform conventional energetic compounds in a number of ways. For example, higher $O_2$ density is provided than obtained with conventional secondary explosives such as ammonium perchlorate. In addition, the novel compounds are highly energetic while not overly impact-sensitive, and are straightforward to synthesize in high yield.

In addition, the compounds of the invention undergo denitration in the body, releasing nitric oxide (NO); the compounds may accordingly be used as pharmaceutical agents, i.e., as so-called "NO-donors." NO donors are useful as vasodilating agents, insofar as NO activates guanylyl cyclase, increasing intracellular levels of cyclic guanosine 3',5'-monophosphate (cGMP), and cGMP brings about smooth muscle relaxation. Previously known NO donors include, for example, nitroglycerin (glyceryl trinitrate), isosorbide dinitrate, isosorbide-5-mononitrate, erythrityl tetranitrate, pentaerythritol tetranitrate, sodium nitroprusside, S-nitroso-N-acetylpenicillamine (SNAP), linsidomine chlorohydrate (also known as SIN-1), and the so-called "NONOates," complexes of nitric oxide and nucleophiles that contain the $N_2O_2^-$ group and release NO upon heating or hydrolysis without need for activation. The pharmacological application of many known NO donors is limited, however, as a result of unwanted side effects, an undesirable NO release profile, or the like. Thus, there is a continuing need in the art for improved pharmaceutical agents useful as vasodilators.

SUMMARY OF THE INVENTION

It is accordingly an object of the invention to address the above-mentioned need in the art by providing novel compounds that are useful as energetic materials, e.g., as high energy oxidizing agents.

It is another object of the invention to provide methods for using the novel compounds as high energy oxidizing agents.

It is still another object of the invention to provide energetic compositions containing one or more of the novel compounds.

It is yet another object of the invention to provide such energetic compositions in the form of propellant formulations, explosive compositions, and the like.

It is a further object of the invention to provide gas-generating compositions containing one or more of the novel compounds.

It is still a further object of the invention to provide methods and compositions for using a compound of the invention as a pharmaceutical agent.

Additional objects, advantages and novel features of the invention will be set forth in part in the description which follows, and in part will become apparent to those skilled in the art upon examination of the following, or may be learned by practice of the invention.

In a first embodiment, the invention relates to novel compounds of formula (I)

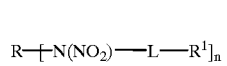

(I)

wherein:
R is either (a) $C_1$–$C_{24}$ hydrocarbyl, optionally substituted with one or more substituents and optionally containing one or more non-hydrocarbyl linkages, e.g., —O—, —S—, —NH—, —N(alkyl)—, —N(NO$_2$)—, —C(O)—, or —C(O)O—, and optionally containing one or more nonhydrogen, noncarbon atoms, e.g., S, Si, B, Al, or the like, (b) —L—R$^1$, where L and R$^1$ are as defined below, or (c) polymeric;

L comprises a divalent hydrocarbylene linking group;

R$^1$ is aromatic, nitrogen-containing heterocyclic, —ONR$^2$R$^3$, —O—[NR$^2$R$^3$R$^4$]$^+$Y$^-$, —ON=CR$^5$R$^6$ or —O—[N=CR$^5$R$^6$]H$^+$Y$^-$ wherein R$^2$, R$^3$ and R$^4$ are independently hydrogen, alkyl, aryl or aralkyl, if alkyl, aryl or aralkyl, optionally substituted with —NO$_2$, —NH$_2$ and/or —NF$_2$ substituents, or wherein R$^2$ and R$^3$ are linked to provide an optionally substituted cyclic moiety, Y$^-$ is an oxidizing anion or a nitrogen-containing heterocyclic anion, and R$^5$ and R$^6$ are independently H, —NH$_2$, —NF$_2$, —NR$^7$—NH$_2$, —NR$^7$—NF$_2$, —NR$^7$CH(NH$_2$)$_2$, —NR$^7$CH(NH$_2$)(NF$_2$), —NR$^7$CH(NF$_2$)$_2$ or —NR$^7$(NO$_2$) wherein R$^7$ is hydrogen, alkyl, aryl or aralkyl, if alkyl, aryl or aralkyl, optionally substituted with —NO$_2$, —NH$_2$ and/or —NF$_2$ substituents, or R$^5$ and R$^6$ can be linked together to form an optionally substituted cycloalkyl ring, and n is an integer indicating the number of —N(NO$_2$)—L— R$^1$ groups bound to R and is thus in the range of 1 to n$_{max}$ wherein n$_{max}$ is the maximum number of substituents that can be bound to R through single covalent bonds.

In another embodiment of the invention, energetic compositions are provided containing one or more of the novel compounds as secondary explosives. These energetic compositions may take any number of forms and have a variety of uses, such as in rocket propellant formulations, including both solid and solution propellants, in liquid monopropellants, in bipropellant and tripropellant compositions, in pyrotechnics, firearms, and the like. In addition, the compounds of the invention are useful in energetic, gas-generating compositions for inflating automotive or aircraft occupant restraint devices. As will be appreciated by those skilled in the art, the aforementioned uses are exemplary in nature and not intended to represent a comprehensive list of possibilities.

In an additional embodiment of the invention, the novel compounds are used as pharmaceutical agents. That is, the compounds of the invention are useful as NO donors and, accordingly, as vasodilators. Methods are thus provided which comprise administration of a compound of the invention to a human or animal, to bring about any effect for which a vasodilator would be useful, e.g., to treat hypertension, angina pectoris, peripheral vascular disease, vasculogenic impotence, and the like. Generally, the compound is administered in a pharmaceutical composition containing a pharmacologically acceptable carrier and, optionally, one or more additional active agents. The compounds may also be useful in increasing the permeability of the so-called "blood-brain barrier" to therapeutic agents.

DETAILED DESCRIPTION OF THE INVENTION

Definitions and Nomenclature:

Before the present compounds, compositions and methods are disclosed and described, it is to be understood that this invention is not limited to specific molecular structures, ligands, or the like, as such may vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a compound of the invention" includes combinations of two or more compounds of the invention, reference to "a secondary explosive" includes combinations of secondary explosives, etc. Similarly, reference to "a nitro group" as in a compound substituted with "a nitro group" includes the possibility of substitution with more than one nitro group, reference to "substituent" includes one or more substituents, and the like.

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like, as well as cycloalkyl groups such as cyclopentyl, cyclohexyl and the like. The term "lower alkyl" intends an alkyl group of 1 to 6 carbon atoms, preferably 1 to 4 carbon atoms.

The term "alkylene" as used herein refers to a difunctional saturated branched or unbranched hydrocarbon chain containing from 1 to 24 carbon atoms, and includes, for example, methylene (—CH$_2$—), ethylene (—CH$_2$—CH$_2$—), propylene (—CH$_2$—CH$_2$—CH$_2$—), 2-methylpropylene (—CH$_2$—CH(CH$_3$)—CH$_2$—), hexylene (—(CH$_2$)$_6$—), and the like. "Lower alkylene" refers to an alkylene group of 1 to 6, more preferably 1 to 4, carbon atoms.

The term "alkenyl" as used herein refers to a branched or unbranched hydrocarbon group of 2 to 24 carbon atoms containing at least one carbon-carbon double bond, such as ethenyl, n-propenyl, isopropenyl, n-butenyl, isobutenyl, y-butenyl, octenyl, decenyl, tetradecenyl, hexadecenyl, eicosenyl, tetracosenyl and the like. Preferred alkenyl groups herein contain 2 to 12 carbon atoms and 1 to 3 carbon-carbon double bonds. The term "lower alkenyl" intends an alkenyl group of 2 to 6 carbon atoms, preferably 2 to 4 carbon atoms, containing one —C=C— bond. The term "cycloalkenyl" intends a cyclic alkenyl group of 3 to 8, preferably 5 or 6, carbon atoms.

The term "alkenylene" refers to a difunctional branched or unbranched hydrocarbon chain containing from 2 to 24 carbon atoms and at least one carbon-carbon double bond. "Lower alkenylene" refers to an alkenylene group of 2 to 6, more preferably 2 to 5, carbon atoms, containing one —C=C— bond.

The term "alkynyl" as used herein refers to a branched or unbranched hydrocarbon group of 2 to 24 carbon atoms containing at least one carbon-carbon triple bond, such as ethynyl, n-propynyl, isopropynyl, n-butynyl, isobutynyl, t-butynyl, octynyl, decynyl and the like. Preferred alkynyl groups herein contain 2 to 12 carbon atoms. The term "lower alkynyl" intends an alkynyl group of 2 to 6, preferably 2 to 4, carbon atoms, and one carbon-carbon triple bond.

The term "alkynylene" refers to a difunctional branched or unbranched hydrocarbon chain containing from 2 to 24 carbon atoms and at least one carbon-carbon triple bond. "Lower alkynylene" refers to an alkynylene group of 2 to 6, more preferably 2 to 5, carbon atoms, containing one carbon-carbon triple bond.

The term "aryl" as used herein refers to an aromatic species containing 1 to 3 aromatic rings, either fused or linked, and either unsubstituted or substituted with 1 or more substituents typically selected from the group consisting of nitro, amino (including primary amino and lower alkyl substituted secondary and tertiary amino), halogen and lower alkyl, where x is an integer in the range of 0 to 6 inclusive as outlined above. Preferred aryl substituents contain 1 aromatic ring or 2 fused aromatic rings. The term "aralkyl" intends a moiety containing both alkyl and aryl species, and will usually be used to refer to aryl-substituted alkyl groups. The term "aralkylene" will be used in a similar manner to refer to moieties containing both alkylene and aryl species, typically intending aryl-substituted alkylene.

The term "arylene" refers to a difunctional aromatic moiety, "monocyclic arylene" refers to a cyclopentylene or phenylene group. These groups may be substituted with up to four ring substituents as outlined above.

The term "heterocyclic" refers to a five- or six-membered monocyclic structure or an eight- to eleven-membered bicyclic heterocycle. Generally, although not necessarily, the heterocyclic substituents herein are aromatic. Each heterocycle consists of carbon atoms and from one to four heteroatoms selected from the group consisting of nitrogen, oxygen and sulfur, with the proviso that the heterocycle contains at least one nitrogen atom. Preferred heterocyclic groups are five-membered rings containing one to four nitrogen atoms, and thus include pyrrole, pyrazole, imidazole, 1,2,3-triazole, 1,2,4-triazole and tetrazole, with 1,2,4-triazole and tetrazole particularly preferred.

"Halo" or "halogen" refers to fluoro, chloro, bromo or iodo, and usually relates to halo substitution for a hydrogen atom in an organic compound. Of the halos, chloro and fluoro are generally preferred.

"Hydrocarbyl" refers to unsubstituted and substituted hydrocarbon radicals containing 1 to about 20 carbon atoms, including linear and branched, saturated and unsaturated species, such as alkyl groups, alkenyl groups, aryl groups, and the like. The term "lower hydrocarbyl" refers to a hydrocarbyl radical containing 1 to about 6 carbon atoms.

"Hydrocarbylene" refers to a difunctional hydrocarbyl radical, where "hydrocarbyl" is as defined above.

The term "polymer" is used in its conventional sense to refer to a compound comprised of two or more monomer units, and is intended to include homopolymers as well as copolymers, and oligomers (typically comprised of at most 20 monomer units) as well as higher molecular weight polymeric entities.

"Optional" or "optionally" means that the subsequently described event or circumstance may or may not occur, and that the description includes instances where said event or circumstance occurs and instances where it does not. For example, the phrase "optionally substituted" aromatic ring means that the aromatic ring may or may not be substituted and that the description includes both an unsubstituted aromatic ring and an aromatic ring bearing one or more substituents.

The term "energetic" to describe the various compounds disclosed and claimed herein is used to refer to a material having a high energy content as represented by an exothermic (negative) heat of combustion. Preferably, the energetic compounds herein also have a positive heat of formation $\Delta H_f$.

As used herein all reference to the Periodic Table of the Elements and groups thereof is to the version of the table published by the Handbook of Chemistry and Physics, CRC Press, 1995, which uses the IUPAC system for naming groups.

The Novel Compounds:

The compounds of the invention are represented by structural formula (I)

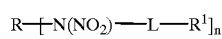

(I)

wherein R, L, $R^1$ and n are as defined earlier herein.

That is, R is either (a) $C_1$–$C_{24}$ hydrocarbyl, optionally substituted with one or more, typically one to six, substituents and optionally containing one or more, typically one to six, non-hydrocarbyl linkages, e.g., —O—, —S—, —NH—, —N(alkyl)—, —N($NO_2$)—, —C(O)—, —C(O)O—, —O—O—, —N=N— or

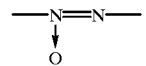

and optionally containing one or more nonhydrogen, noncarbon atoms, e.g., S, Si, B or Al, (b) —L—$R^1$, where L and $R^1$ are as defined below, or (c) polymeric;

L comprises a divalent hydrocarbylene linking group;

$R^1$ is aromatic, nitrogen-containing heterocyclic, —$ONR^2R^3$, —O—[$NR^2R^3R^4$]$^+Y^-$, —ON=$CR^5R^6$ or —O—[N=$CR^5R^6$]$H^+Y^-$ wherein $R^2$, $R^3$ and $R^4$ are independently hydrogen, alkyl, aryl or aralkyl, if alkyl, aryl or aralkyl, optionally substituted with —$NO_2$, —$NH_2$ and/or —$NF_2$ substituents, or wherein $R^2$ and $R^3$ are linked to provide an optionally substituted cyclic moiety, $Y^-$ is an oxidizing anion or a nitrogen-containing heterocyclic anion, and $R^5$ and $R^6$ are independently H, —$NH_2$, —$NF_2$, —$NR^7$—$NH_2$, —$NR^7$—$NF_2$, —$NR^7CH(NH_2)_2$, —$NR^7CH(NH_2)(NF_2)$, —$NR^7CH(NF_2)_2$ or —$NR^7(NO_2)$ wherein $R^7$ is hydrogen, alkyl, aryl or aralkyl, if alkyl, aryl or aralkyl, optionally substituted with —$NO_2$, —$NH_2$ and/or —$NF_2$ substituents, or $R^5$ or $R^6$ can be linked together to form an optionally substituted cycloalkyl ring; and n is an integer defining the number of —N($NO_2$)—L—$R^1$ groups bound to R, and thus is in the range of 1 to $n_{max}$, wherein $n_{max}$ is the maximum number of substituents that can be bound to R through single, covalent bonds.

Examples of R radicals include, but are not limited to, carbyl, methylene, methyl, ethylene, ethyl, ethenylene, ethenyl, ethynylene, ethynyl, trimethylene, propylene, n-propyl, isopropyl, 1-propynyl, 2-propynyl, cyclopropyl, 1,2,3-propanetriyl, allyl, tetramethylene, n-butyl, 1,3-butadienyl, 1-butenyl, 2-butenyl, 3-butenyl, 2-butenylene, cyclobutyl, pentamethylene, 1-pentenylene, pentyl, pentenyl, cyclopentyl, cyclopentenyl, cyclopentylene, cyclohexyl, cyclohexenyl, cyclohexylene, cyclohexenylene, hexyl, hexamethylene, heptyl, octyl, 1,1,3,3-tetramethylbutyl, nonyl, nonylene, decyl, decylene, undecyl, undecylene, cetyl, octadecanoyl, phenyl, phenylene, phenylenedimethylene, phenethyl, phenylethylene, xylylene, benzyhydryl, biphenyl, biphenylyl, naphthyl, naphthylene, napthylmethylidene, pyranyl, pyrrolidinyl, morpholino, thiazolyl, tetracosyl, —$CH_2$—O—$CH_2$—, —$CH_2$—S—$CH_2$—, and the like. R may be unsubstituted or substituted, if substituted, generally having 1 to 6, more typically 1 to 3, substituents such as lower alkyl, lower alkenyl, lower alkynyl, amino, lower alkyl-substituted amino, di(lower alkyl) amino, nitro, halo, halogenated lower alkyl, halogenated amino (e.g., $NF_2$), —$NR^7(NO_2)$ wherein $R^7$ is as defined previously, or the like. Preferred R radicals are $C_1$–$C_6$ hydrocarbyl groups, e.g., carbyl, methylene, ethylene, ethenylene, dimethylethylene, propylene, etc., and —L—$R^1$.

R, as noted above, may also be polymeric, such that the —N(NO$_2$)—L—R$^1$ groups are pendant to a polymer backbone. The polymer backbone may comprise a polyolefin such as polyethylene, polypropylene or polyisoprene, a halogenated polymer such as polytrifluoroethylene, poly (vinyl fluoride) or poly(vinylidene chloride), a cellulosic polymer such as ethyl cellulose or hydroxypropyl cellulose, a nitrogenous polymer such as polyethyleneimine, a polyamine or a polyamide, or a polyglycol such as polyoxymethylene or poly(ethylene oxide). The —N(NO$_2$)—L—R$^1$ groups are preferably introduced prior to polymerization, i.e., they are present on the monomeric species used to create the polymer. For example, poly (ethylene oxide) having —N(NO$_2$)—L—R$^1$ pendant groups may be prepared by ring-opening polymerization of the substituted epoxide

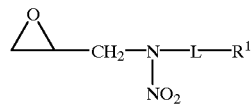

and, similarly, polyethylene having pendant —N(NO$_2$)—L—R$^1$ groups may be prepared by addition polymerization of the substituted olefin

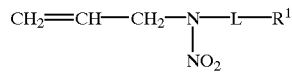

Alternatively, pendant —N(NO$_2$)—L—R$^1$ groups may be introduced into an intact polymer by reaction with functional groups present therein, e.g., —CH$_2$Cl, —CH$_2$NH$_2$ or the like.

L may be, for example, alkylene, alkenylene, alkynylene, typically lower alkylene, lower alkenylene or lower alkynylene, arylene, alkarylene, aralkylene, optionally substituted with amino, nitro, lower alkyl and/or halogen substituents and/or containing —O—, —S—, —N(alkyl)—, etc. As long as "L" inserts at least one atom between the N-nitro group and —R$^1$ to provide spacing therebetween, and as long as there are no electron-withdrawing groups alpha to the oxygen atom bound to the N-nitro linkage, there are no limitations on the identity of L, and L may be any of the bifunctional substituents listed above as "R" groups. However, typical linking groups suitable as "L" are lower alkylene, lower alkenylene, including cyclic lower alkylene and cyclic lower alkenylene, and monocyclic arylene, including monocyclic aromatic heterocycles, e.g., methylene, ethylene, n-propylene, ethenylene, tetramethylene, cyclohexylene, phenylene, etc.

Specific R$^1$ groups include, but are not limited to, —ONH$_2$, —ON(CH$_3$)$_2$, —ONH(CH$_3$), —ONH(CH$_2$CH$_3$), —ON(CH(CH$_3$)$_2$), —ON=C(NH$_2$)$_2$, —ON=C(NF$_2$)$_2$, —ON=C(NH—NH$_2$)$_2$, —ON=C(H)NH$_2$, —ON=C(H)—NH—NH$_2$, —ON=C(NH$_2$)—NH—NH$_2$, —ON=C(H)NH—CH(NH$_2$)$_2$, —ON=C(NH$_2$)(NHNO$_2$), —ONH$_3$$^+$ Y$^-$, —ON(CH$_3$)$_3$$^+$Y$^-$, —ON(CH$_2$CH$_3$)$_3$$^+$Y$^-$, —O—[N=C(NH$_2$)$_2$•H$^+$]Y$^-$, —O—[N=C(NF$_2$)$_2$•H$^+$]Y$^-$, —O—[N=C(NH—NH$_2$)$_2$•H$^+$]Y$^-$, —O—[N=C(H)NH$_2$•H$^+$]Y, —O—[N=C(H)—NH—NH$_2$•H$^+$]Y$^-$, —O—[N=C(NH$_2$)—NH—NH$_2$•H$^+$]Y$^-$, —O—[N=C(H)NH—CH(NH$_2$)$_2$•H$^+$]Y, —O—[N=C(NH$_2$)(NHNO$_2$)•H$^+$]Y$^-$,

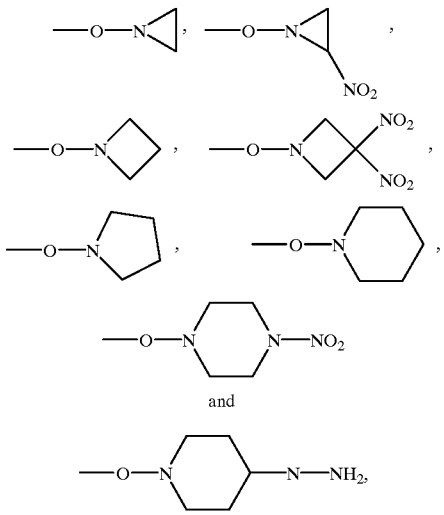

and wherein Y$^-$ is any anion useful to provide oxidizing capability in an energetic composition, including nitrate, chlorate, perchlorate, hexafluorophosphate, N(NO$_2$)$_2$$^-$, C(NO$_2$$^-$)$_3$$^-$, halogen anions, and the like. Additional R$^1$ groups are nitrogen-containing heterocycles, including pyrrole, pyrazole, imidazole, 1,2,3-triazole, 1,2,4-triazole, tetrazole, indazole, quinazoline, and the like, either unsubstituted or substituted on a ring carbon and/or nitrogen with a substituent such as amino, nitro, lower alkyl or halogen.

The integer "n" indicating the number of —N(NO$_2$)—L—R$^1$ groups that are bound to R, is at least 1, but may be 2, 3, . . . and up to n$_{max}$, wherein n$_{max}$ indicates the maximum number of substituents that can be bound to R through single covalent bonds. For example, when R is —L—R$^1$, n$_{max}$ is 1 and n is 1. When R is —CH$_3$, n$_{max}$ is 1 and n is 1. When R is C, n$_{max}$ is 4 and n is 1, 2, 3 or 4. When R is —CH=CH—, n$_{max}$ is 2 and n can be 1 or 2. In the latter two cases, obviously R will have to have n$_{max}$—n substituents that are not shown, which will generally be hydrogen, alkyl, amino, alkyl-substituted amino, including mono-substituted alkylamino and dialkylamino, halogenated amino, or alkyl substituted with amino, halogenated amino, nitro, or other nitrogen-containing groups; typically, the remaining (n$_{max}$—n) substituents are hydrogen, lower alkyl, amino, lower alkyl(amino), di(lower alkyl) amino, or nitro-substituted lower alkyl.

Representative compounds encompassed by generic structure (I) are as follows:

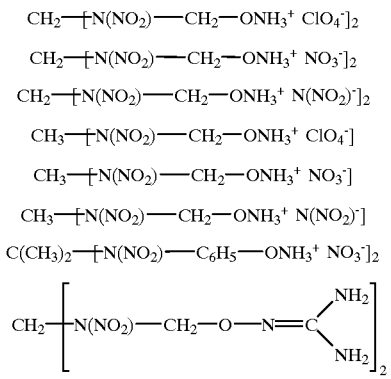

-continued

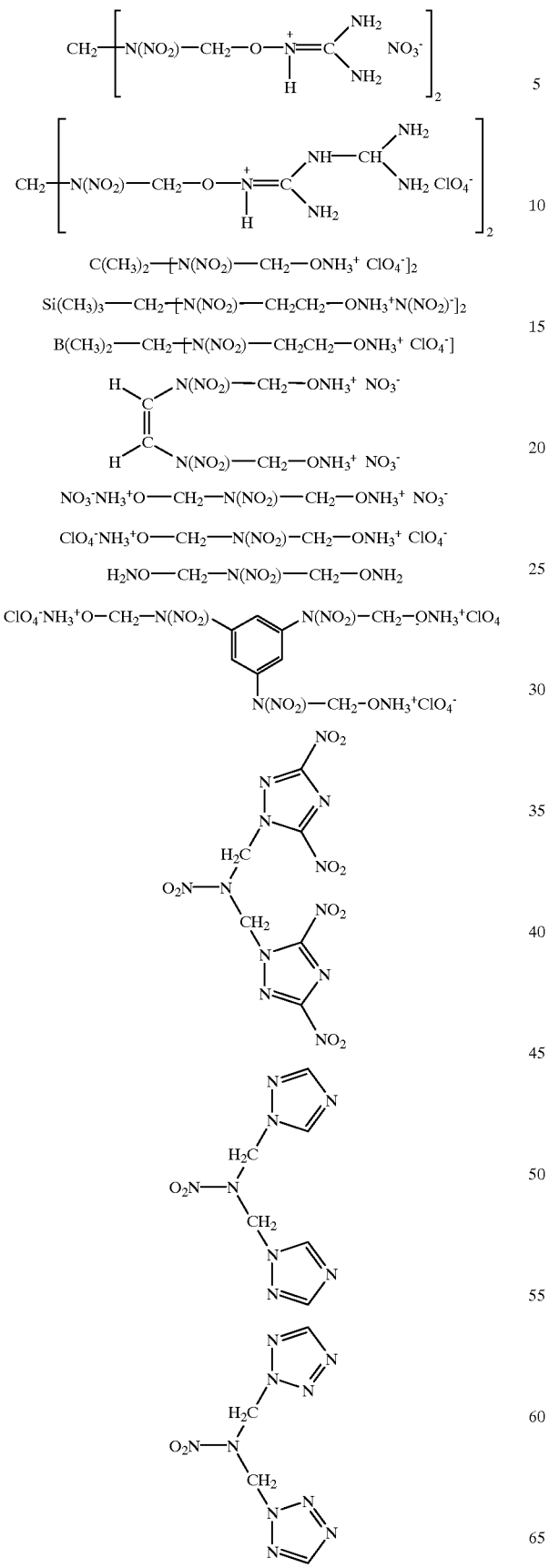

-continued

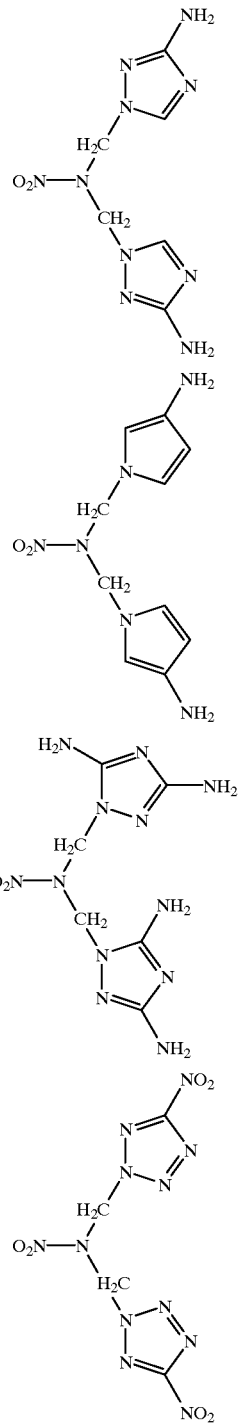

Energetic Compositions:

Gas-generating compositions for inflating airbags or for other uses contain a compound of the invention as discussed earlier herein, an igniter material, and, optionally, an additional oxidizer. "Igniter materials," as appreciated by those skilled in the art, are compounds that act as primary explosives in an energetic composition. Preferred igniter compounds for use herein are thermally stable, typically up to a temperature of at least about 150° C.; the compounds should also have a relatively high heat of formation, and be safe, economical and straightforward to synthesize in relatively high yield. Conventional igniters such as lead azide and lead styphnate may be used, although preferred igniters are the N,N'-azobis-nitroazoles described in commonly assigned U.S. patent application Ser. No. 09/078,302, filed May 13, 1998 for "N,N-AZOBIS-NITROAZOLES AND ANALOGS THEREOF AS IGNITER COMPOUNDS FOR USE IN ENERGETIC COMPOSITIONS" by Bottaro et al. Examples of additional oxidizers that may be incorporated into the present gas-generating compositions include, but are not limited to, ammonium nitrate (AN), phase-stabilized ammonium nitrate (PSAN), ammonium dinitramide (AND), potassium nitrate (KN), potassium dinitramide (KDN), sodium peroxide ($Na_2O_2$), ammonium perchlorate (AP), and KDN—AN, a cocrystallized form of potassium dinitramide and ammonium nitrate.

The aforementioned gas-generating compositions may also, if desired, contain a gas-generating fuel and a binder. Suitable gas-generating fuels include triaminoguanidine nitrate (TAGN), diaminoguanidine nitrate (DAGN), monoaminoguanidine nitrate (MAGN), 3-nitro-1,2,4-triazole-5-one (NTO), salts of NTO, urazole, triazoles, tetrazoles, guanidine nitrate, oxamide, oxalyldihydrazide, melamine, various pyrimidines, semicarbazide ($H_2N$—(CO)—$NHNH_2$), azodicarbonamide ($H_2N$—(CO)—N=N—(CO)—$NH_2$), and mixtures thereof. Suitable binders are generally organic polymeric materials, e.g., polycarbonates, polyesters, polyurethanes and the like.

Another area of interest is in the manufacture of rocket propellant compositions, including solid and solution propellants, typically solid propellants. Such compositions will contain, in addition to a secondary explosive comprising a compound of the invention and an igniter material, a binder and fuel. Examples of binder materials for use in propellant applications include but are not limited to polyoxetanes, polyglycidyl azide, hydroxyl-terminated polybutadiene, polybutadiene-acrylonitrileacrylic acid terpolymer, polyethers, polyglycidyl nitrate, and polycaprolactone; see, e.g., U.S. Pat. No. 5,292,387 to Highsmith et al. Suitable propellant fuels will generally be metallic, e.g., aluminum, beryllium, boron, magnesium, zirconium, or mixtures or alloys thereof. Other components for incorporation into propellant compositions include plasticizers, burn rate modifiers, ballistic additives, and the like.

The present compounds may also be used as the liquid oxidizer component of bipropellant and tripropellant compositions, without need for additional oxidizing agents. In addition, the compounds are useful in pyrotechnic applications, in firearms, and the like. If desired, the compounds of the invention may be combined with other secondary explosives, including, but not limited to, 2,4,6-trinitrotoluene (TNT), cyclo-1,3,5-tri-methylene-2,4,6-trinitramine (RDX or cyclonite), high melting explosives (HMX), and picric acid.

Pharmaceutical Applicability:

The compounds of the invention are also useful as pharmaceutical agents. In one embodiment, methods and compositions for treating NO-responsive disorders and conditions in a human or animal are provided. That is, the compounds of the invention, by virtue of the N-nitro group, undergo denitration in the body and are for that reason useful as NO donors and thus as vasodilating agents.

The invention thus encompasses methods for using the novel compounds as vasodilators, e.g., in treating moderate to severe hypertension, in providing acute relief of angina pectoris, for long-term prophylactic management of angina pectoris, to produce controlled hypotension during surgical procedures, for the treatment of ischemic pain, to treat pulmonary edema associated with acute myocardial infarction, to treat or prevent vasculogenic impotence, to treat peripheral vascular disease, to treat esophageal disorders such as achalasia and esophageal spasm, to facilitate endoscopic removal of gallstones, and in obstetrics, e.g., in inducing uterine relaxation to prolong pregnancy and manage premature labor.

The compounds may be administered via the oral, parenteral (including subcutaneous, intravenous and intramuscular injection), nasal, buccal, sublingual, urethral, rectal, vaginal, cutaneous, or transdermal routes, and the composition and carrier are to be selected accordingly. For compounds of the invention that are orally active, oral administration is preferred. The amount of compound administered will, of course, be dependent on the indication, the subject being treated, the subject's weight, the mode of administration, and the judgment of the prescribing physician. Typically, however, dosage will be at most 10% of the $LD_{50}$ for any one compound, and will generally be in the range of approximately 0.01 mg/kg/day to 2.0 mg/kg/day, preferably in the range of about 0.1 mg/kg/day to 1.0 mg/kg/day. Suitable dosages will generally be analogous to dosages employed for known nitrovasodilators such as nitroglycerin, sodium nitroprusside, isosorbide dinitrate, and the like.

The compounds will generally be administered in a pharmaceutical composition containing an effective amount of the active compound and a pharmacologically acceptable excipient suited to the particular mode of administration. The compositions may also include other pharmaceutical agents, adjuvants, diluents, buffers, etc. Depending on the intended mode of administration, the pharmaceutical compositions may be in the form of solid, semi-solid or liquid dosage forms, such as, for example, tablets, suppositories, pills, capsules, powders, liquids, suspensions, or the like, preferably in unit dosage form suitable for single administration of a precise dosage.

The compounds also find pharmaceutical utility in increasing the permeability of the "blood-brain barrier" to therapeutic agents. While not unambiguously defined in anatomical terms, the blood-brain barrier is accepted as a boundary between the periphery and the central nervous system (CNS), serving as a barrier to the passive diffusion of substances from the bloodstream into various regions of the CNS. There is an ongoing need for compounds that increase permeability of the blood-brain barrier to enhance the efficacy of various drugs, e.g., chemotherapeutic agents or the like, that are used to treat infectious or tumors localized in the brain. The present compounds are useful in this regard.

Synthesis and Manufacture:

The compounds of the invention may be readily synthesized in a variety of ways using techniques that are relatively straightforward and readily scaled up. Representative synthetic methods are described in Examples 1 through 5 below.

Synthetic details not explicitly disclosed will be within the knowledge of or may readily deduced by those skilled in the art of synthetic organic chemistry, or may be found in the relevant texts such as Kirk-Othmer's *Encyclopedia of Chemical Technoloy*, House's Modern *Synthetic Reactions*, C. S. Marvel and G. S. Hiers' text, ORGANIC SYNTHESIS, Collective Volume 1, or in T. L. Gilchrist, *Heterocyclic Chemistry*, 2nd Ed. (New York: John Wiley & Sons, 1992) or the like. Synthesis of representative compounds is exemplified below.

Manufacture of gas-generating compositions, propellants and other energetic compositions may be carried out using conventional means, as will be appreciated by those skilled in the art. A suitable method for preparing anhydrous gas-generating composition is disclosed, for example, in U.S. Pat. No. 5,473,647 to Blau et al. and in international patent publication WO 95/00462 (Poole et al.). Of course, other methods for manufacture may be used as well. Such methods are described in the pertinent literature or will be known to those familiar with the preparation of energetic compositions.

EXPERIMENTAL

The following examples are put forth so as to provide those of ordinary skill in the art with a complete disclosure and description of how to prepare and use the compounds disclosed and claimed herein. Efforts have been made to ensure accuracy with respect to numbers (e.g., amounts, temperature, etc.) but some errors and deviations should be accounted for. Unless indicated otherwise, parts are parts by weight, temperature is in °C. and pressure is at or near atmospheric.

All patents, patent applications, journal articles and other references mentioned herein are incorporated by reference in their entireties.

EXAMPLE 1

Synthesis of 1,5 di(aminoxy)-2, 4-dinitraazapentane, $CH_2[N(NO_2)CH_2ONH_2]_2$:

(a) $CH_2[N(NO_2)CH_2ONC(OHC_2CH_3)CH_3]_2$: Ethyl-N-hydroxyacetamidate (4.05 g, 39 mmol) (Aldrich) was combined with $CH_3CN$ (175 mL) in a 3-neck 250 mL flask. One equivalent of KOH (85%, 2.49 g, 39 mmol) ground to a fine powder was then added to the solution which was warmed to 68°C. for 30 min. Then $CH_2[N(NO_2)CH_2Cl]_2$ (4.0 g, 19.5 mmol; prepared using the methodology set forth in U.S. Pat. No. 3,883,374 to Rosher) dissolved in $CH_3CN$ (20 mL) was added to this mixture over 10 min. After addition and stirring at 68° C. for 30 min. the slurry was cooled to ambient temperature and filtered over a medium glass frit. The filtered solid was dissolved in water (30 mL) and extracted with diethyl ether ($Et_2O$) (3×100 mL). Removal of the solvent from the filtrate in vacuo produced a yellow-brown oil that was dissolved in 140 mL $Et_2O$ and washed with water (3×30 mL). All ether fractions were combined and dried over $Na_2SO_4$. Concentration and cooling to −20° C. produced 1.27 g of crystalline product. Repeat of this procedure produced 0.75 g more product giving a combined yield of 2.02 g, 31%, m.p. 71–74° C. $^1H$ NMR (DMSO, 30° C.) 5.85 (s, 2H), 5.6 (s, 4H), 3.92 (q, 4H), 1.9 (s, 6H), 1.2 (t, 6H).

(b) $CH_2[N(NO_2)CH_2ONH_2]_2$: $CH_2[N(NO_2)CH_2ONC(OHC_2CH_3)CH_3]_2$ (1.00 g, 2.96 mmol), prepared in part (a), was suspended in absolute EtOH (30 mL). HCl (37%, 0.58 g, 14.7 mmol) was added to this solution at 25° C. The reaction was slow until the mixture was warmed to 50° C. and the dihydrochloride salt of $CH_2[N(NO_2)CH_2ONH_2]_2$ precipitated. After stirring for 1 h the solid was isolated by filtration and rinsed with EtOH and then $Et_2O$. Yield 0.71 g, 80%. The salt (0.6 g, 2.0 mmol) was suspended in absolute EtOH (40 mL) and KOH solution (0.5 g of 85% KOH in 30 mL of EtOH) was used to neutralize to a pH of 8. The KCl was removed by filtration and the solvent removed from the filtrate to give 0.25 g of product. Further rinsing of the KCl solid gave more product, 0.15 g. Combined yield: 0.35 g, 77% m.p. 90–95° C. $^1H$ NMR (DMSO, 30° C.) 6.6 (s, 4H), 5.88 (s, 2H), 5.3 (s, 4H).

EXAMPLE 2

Synthesis of 1,3 di(aminoxy)-2-nitraazapropane, $O_2NN[CH_2ONH_2]_2$:

(a) $O_2NN[CH_2ONC(OCH_2CH_3)CH_3]_2$: Ethyl-N-hydroxyacetamidate (3.89 g, 38 mmol) was dissolved in $CH_3CN$ (150 mL) in a 3-neck 200 mL flask. KOH (85%, 2.49 g, 38 mmol) ground to a fine powder was then added to the solution which was warmed to 68° C. for 30 min. The solution was cooled to ambient temperature and added via large bore cannulae to $O_2NN[CH_2Cl]_2$ (prepared using the methodology of U.S. Pat. No. 4,085,123 to Flanagan) in $CH_3CN$ (75 mL). The color of the resulting solution was yellow-orange and a fine white precipitate was observed. The mixture was heated at 65° C. for 1 hr, cooled to ambient temperature over 30 min and filtered. Removal of solvent in vacuo produced a yellow oil that dissolved in $Et_2O$ (30 mL) and was washed with water (3×20 mL.) After drying the $Et_2O$ layer over $Na_2SO_4$ all solvent was removed in vacuo. The oily residue was distilled and product collected at 120° C. ($10^{-2}$ torr). Yield: 3.42 g, 62% m.p. 63° C. $^1H$ NMR ($CDCl_3$, 30° C.) 5.6 (s, 4H), 1.97 (s, 6H), 1.3 (t, 6H).

(b) $O_2NN[CH_2ONH_2]_2$: $O_2NN[CH_2ONC(OCH_2CH_3)CH_3]_2$ (1.96 g, 6.7 mmol), prepared in part (a) of this example, was dissolved in absolute EtOH (40 mL). HCl (37%, 1.44 g, 14.7 mmol) was added to this solution and after stirring for 2 hours all volatiles were removed leaving a solid residue. This dihydrochloride salt of $O_2NN[CH_2ONH_2]_2$ was washed with $Et_2O$ (2×20 mL) and dried in vacuto. The yield was assumed quantitative. The solid was transferred to a flask, suspended in absolute EtOH (30 mL) and neutralized to a pH of 8 with a premade KOH solution (1.0 g 85% KOH in 20 mL of EtOH). The KCl was removed by filtration and the mother liquor concentrated in vacuo to give a waxy solid product (0.92 g, 90%). The $O_2NN[CH_2ONH_2]_2$ may be recrystallized from EtOH with significant losses. m.p. 63° C. $^1H$ NMR (DMSO, 30° C.) 6.45 (s, 4H), 5.27 (s, 4H).

EXAMPLE 3

Synthesis of $O_2NN[CH_2ONH_3^+]_2 [ClO_4^-]_2$:

$O_2NN[CH_2ONH_2]_2$ (0.52 g, 3.42 mmol), prepared in Example 2, was dissolved in absolute EtOH (20 mL) and cooled to 0° C. Perchloric acid (70%, 0.98 g, 6.84 mmol) was then added dropwise and the solution stirred at ambient for 20 min. Drierite (3 g, presaturated with EtOH) was added and the slurry was stirred for 20 min. and filtered. The filtrate was then concentrated to 2 mL and $Et_2O$ (5 mL) was layered carefully on top of the solution. After 48 h crystals appeared and were isolated by filtration, washed with $Et_2O$ (20 mL), and dried in vacuo. Yield: 0.4 g, 33%. m.p. 150° C. $^1H$ NMR (DMSO, 30° C.) 5.4 (s, 4), 3.5 (brs).

EXAMPLE 4

Synthesis of $O_2NN[CH_2ONH_3^+]_2 [NO_3^-]_2$:

$O_2NN[CH_2ONH_2]_2$ (1.0 g, 6.57 mmol), prepared in Example 2, was dissolved in absolute EtOH (40 mL) and cooled to 0° C. Two equivalents of nitric acid (100%, 0.83 g, 13.1 mmol) was then added dropwise and the solution stirred at ambient temperature for 20 min. The solution was then concentrated to 10 mL and cooled to −20° C. over 48 h. The solid was isolated by filtration and dried in vacio. Yield: 1.0 g, 54%. m.p. 125° C. $^1H$ NMR (DMSO, 30° C.) 5.6 (s).

EXAMPLE 5

Synthesis of 1,1'-(2-Nitraza-1,3-propanediyl)-3,5-dinitro-1,2,4-triazole:

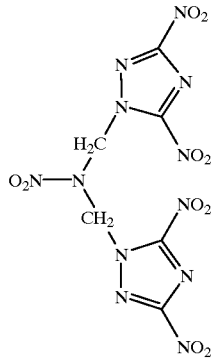

Sodium dinitro-1,2,4-triazole (3.6 g, 20 mmol; prepared from the ammonium salt, in turn synthesized using the method of Stinecipher (M. M. Stinecipher (1982), "Eutectic Composite Explosives Containing Ammonium Nitrate," *Proceedings of the 7th International Symposium on Detonation* (Annapolis, Md.), at pp. 801–810), was suspended in 30 mL of dry acetonitrile. 2-Nitraza-1,3-dichloropropane (1.6 g, 10 mmol) was added, and the resulting mixture was stirred at 60° C. in a sealed vessel for 15 hours. The acetonitrile was evaporated ill vacuo, and the resulting residue was partitioned between 75 mL of ethyl acetate and 100 mL of $H_2O$. The aqueous layer was discarded, and the organic layer was washed with 2×100 mL of 0.5 M $Na_2HPO_4$. The organic layer was then passed through a 1" by 2" plug of silica gel, washing with ethyl acetate. The effluent was concentrated in vacuo and crystallized from ethyl acetate/isopropanol to give 4 g (90%) of the desired product, mp 195° C. (explodes at 200° C.) as a white microcrystalline powder. $^1H$ NMR ($CD_3CN$) δ 7.1 ppm (singlet).

What is claimed is:

1. A compound having the structural formula (I)

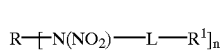

wherein:

n is 1;

R is —L—$R^1$;

L is a lower alkylene linking group; and $R^1$ is a 1,2,4-triazole bound to L through a ring nitrogen atom, and is optionally substituted with a substituent selected from the group consisting of amino, alkylamino, dialkylamino, nitro, alkyl and halogen.

2. The compound of claim 1, wherein $R^1$ is substituted on at least one carbon atom with a nitro group.

3. The compound of claim 1, having the structural formula

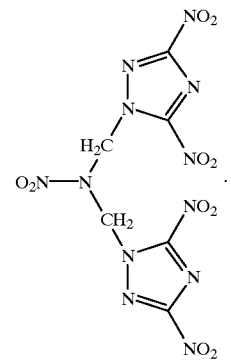

4. The compound of claim 1, having the structural formula

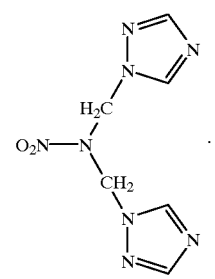

5. The compound of claim 1, having the structural formula

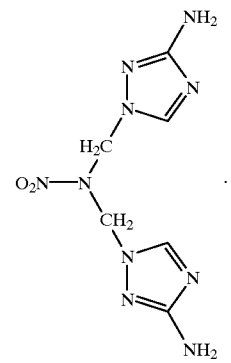

6. The compound of claim 1, having the structural formula

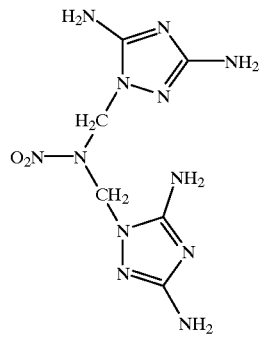

7. A pharmaceutical composition comprising a therapeutically effective amount of the compound of claim 1 in combination with a pharmaceutically acceptable carrier.

8. The pharmaceutical composition of claim 7, in the form of a solid.

9. The pharmaceutical composition of claim 1, in unit dosage form.

10. The compound of claim 1, wherein L is methylene.

* * * * *